(12) United States Patent
Karpol et al.

(10) Patent No.: US 6,466,315 B1
(45) Date of Patent: Oct. 15, 2002

(54) METHOD AND SYSTEM FOR RETICLE INSPECTION BY PHOTOLITHOGRAPHY SIMULATION

(75) Inventors: Avner Karpol, Ziona; Boaz Kenan, Rehovot, both of (IL)

(73) Assignee: Applied Materials, Inc., Santa Clara, CA (US)

(*) Notice: Subject to any disclaimer, the term of this patent is extended or adjusted under 35 U.S.C. 154(b) by 0 days.

(21) Appl. No.: 09/390,503

(22) Filed: Sep. 3, 1999

(51) Int. Cl.$^7$ .............................................. C01N 21/88
(52) U.S. Cl. ................... 356/237.4; 356/237.5
(58) Field of Search ................ 356/237.2, 237.3, 356/237.4, 237.5

(56) References Cited

U.S. PATENT DOCUMENTS

| | | | |
|---|---|---|---|
| 3,725,574 A | 4/1973 | Gast | 178/6.7 R |
| 4,595,289 A | 6/1986 | Feldman et al. | |
| 4,926,489 A | 5/1990 | Danielson et al. | 382/8 |
| 5,210,635 A | 5/1993 | Nagata et al. | 359/198 |
| 5,264,912 A * | 11/1993 | Vaught et al. | 356/237.5 |
| 5,481,624 A * | 1/1996 | Kamom | 356/237.5 |
| 5,563,702 A | 10/1996 | Emery et al. | 356/73 |
| 5,795,688 A | 8/1998 | Burdorf et al. | 430/30 |
| 5,838,433 A | 11/1998 | Hagiwara | 356/237 |
| 6,023,328 A * | 2/2000 | Pierrat | 356/237.4 |

FOREIGN PATENT DOCUMENTS

EP  628 806 A2  12/1994

OTHER PUBLICATIONS

Richard A. Ferguson et al., "Application of an Aerial Image Measurement System to Mask Fabrication and Analysis", SPIE vol. 2087 Photomask Technology and Management (1993) pp. 131–144.
R. Martino et al., "Application of the Aerial Image Measurement System (AIMS™ to the Analysis of Binary Mask Imaging and Resolution Enhancement Techniques", SPIE vol. 2197, pp. 573–584.

* cited by examiner

Primary Examiner—Richard A. Rosenberger
(74) Attorney, Agent, or Firm—Sughrue Mion Zinn MacPeak & Seas, LLP.

(57) ABSTRACT

A system and method are presented for optical inspection of reticles by simulating the operation of a selected stepper. The system utilizes a flying spot inspection technique and includes a scanning apparatus and a detection unit. The scanning apparatus uses a laser source similar to that of the stepper of interest. First and second light directing assemblies are accommodated in the optical paths of, respectively, incident and transmitted light, and are designed so as to provide coherence of the light substantially equal to that of the stepper.

17 Claims, 3 Drawing Sheets

METHOD AND SYSTEM FOR RETICLE INSPECTION BY PHOTOLITHOGRAPHY SIMULATION

FIELD OF THE INVENTION

The present invention is in the field of automatic optical inspection techniques, and relates to a method and system for inspecting reticles or masks in a manner to simulate the operation of a specific photolithography tool in which this reticle is to be used.

BACKGROUND OF THE INVENTION

Photolithography is one of the principal processes in the manufacture of semiconductor devices, and consists of patterning the wafer's surface in accordance with the circuit design of the semiconductor devices to be produced. More specifically, a circuit design to be fabricated on the wafer is first patterned on a mask or reticle (for simplicity, the terms mask and reticle will be used here interchangeably, although in actuality they refer to somewhat different techniques). The wafer is coated with a photoresist material, and is then placed in a photolithography tool to be exposed to light passing through the reticle to produce a latent image of the reticle on the photoresist material. Thereafter, the exposed photoresist material is developed to produce the image of the mask on the wafer. After the completion of the photolithography process, the uppermost layer of the wafer is etched, a new layer is deposited, and the photolithography and etching operations are started again. In this repetitive manner, a multi-layer semiconductor wafer is produced.

As is well known, photolithography tools utilize a lamp or a laser as a light source, and utilize a relatively high numerical aperture (NA) objective to achieve a relatively high resolution. The optics of such tools are generally designed to produce reduction (negative magnification) of the image of the reticle, e.g., ⅕ onto the wafer. Different models use different NA and magnification combination, as designed by the manufacturer of the tool.

It should be appreciated that in order to obtain operating semiconductor devices, the reticle must be defect free. Moreover, in most modern processes, the reticle is used in a repeated manner to create many dies on the wafer. Thus, any defect on the reticle will be repeated multiple times on the wafer and will cause multiple devices to be defective. Therefore, various reticle inspection tools have been developed and are available commercially. One type of such inspection systems, to which this invention pertains, scans the entire reticle using an illumination spot technique to inspect the reticle for defects. Examples of such systems are provided in U.S. Pat. Nos. 4,926,489, 5,838,433, and 5,563,702, and an example is schematically depicted in FIG. 1.

As shown in FIG. 1, a reticle 10 is placed on an x-y stage 20. A laser 30 produces an illumination beam of a relatively narrow diameter. A scanner 40, e.g., a rotating mirror or an acousto-optic deflector (AOD), is used to scan the beam in one direction, generally referred to as the "fast scan" direction. The stage 20 is moved in a direction perpendicular to the fast scan direction in a serpentine manner, so that the entire surface of the reticle is scanned. The scanned beam passes through the dichroic mirror 50 and is focused by objective lens 60 onto the reticle. Light transmitted through the reticle 10 is collected by the objective lens 70 and focused onto light sensor 80, e.g., a photo-multiplier tube (PMT). Reflected light is deflected by the dichroic mirror 50 to be collected by the lens 95 and focused onto the light sensor 90. Shown by a dotted line is an optional optics and tilted mirror assembly that can be used to obtain an interferometer image of the reticle for inspection of phase shift designs (see, e.g., the cited U.S. Pat. No. '702).

Conceptually, the inspection systems exemplified in FIG. 1 generate a highly magnified image of the reticle. Each pixel in the image corresponds to a sampled illuminated spot on the reticle, and has a grey level corresponding to the amount of light received by the light sensor. This grey level can be either compared to a corresponding pixel from an adjacent die on the reticle, or binarized and compared. to a database or compared to a gray scale image calculated from the database. When a discrepancy above a designated threshold is encountered, the location is identified as suspected of having a defect.

Recent advancements in photolithography technology have introduced another factor which may cause the latent image on the wafer to be defective. Specifically, the reduction in design rules necessitates various measures to counter changes in the latent image caused by the interaction of the light with the design on the reticle. Such interactions are generally referred to as "optical proximity effects", and result in, for example, corner rounding, a difference between isolated and semi-isolated or dense patterns, a lack of CD linearity, etc. Whilst not being detected as potential defects. in a particular reticle by the conventional inspection system, these effects could produce real defects on the wafer. On the other hand, these effects should not cause the system to issue an alarm if they will not be transferred as defects onto the wafer. Moreover, there is a need to inspect the countermeasures, such as optical proximity correction OPC and phase shift etching on reticles, and test their design and effectiveness.

Conventionally, in designing and evaluating reticles, especially advanced reticles having OPC and phase shift features, one has to create the reticle, expose a wafer using the reticle, and check that the features of the reticle have been transferred to the wafer according to the design. Any variations in the final features from the intended design necessitate modifying the design, creating a new reticle, and exposing a new wafer. Needless to say, such a process is expensive, tedious, and time consuming. In order to short-cut this process, and to assist in design and evaluation of advanced reticles, IBM has recently developed a microscope called the Aerial Image Measurement System (AIMS).

The AIMS system is disclosed, for example, in European Patent Publication No. 0628806, and in the following articles: Richard A. Ferguson et al. "*Application of an Aerial Image Measurement System to Mask Fabrication and Analysis*", SPIE Vol. 2087 *Photomask Technology and Management* (1993) pp. 131–144, and R. Martino et al. "*Application of the Aerial Image Measurement System* (AIMS™) *to the Analysis of Binary Mask Imaging and Resolution Enhancement Techniques*", SPIE Vol. 2197 pp. 573–584. The Microscope is available commercially from Carl Zeiss, GmbH of Germany, under the trade name MSM100 (standing for Microlithographhy Simulation Microscope).

Conceptually, rather than obtaining a highly magnified image of the reticle, as is done by inspection systems, the AIMS system emulates a stepper and creates a highly magnified image of the latent image produced by the reticle. Specifically, the operational parameters of illumination and light collection in the AIMS, such as wavelength and NA, can be adjusted by the user to simulate the tool which will be used to expose wafers using the reticle. The illumination is provided in a manner which simulates exposure in a stepper, so that a latent image of the reticle is created.

However, rather than placing a wafer at the location of the latent image, a sensor is placed so as to produce an aerial image of the latent image produced by the reticle. Also, rather than providing reduction of the image like a stepper, the AIMS magnifies the latent image to enable easier image acquisition.

The AIMS is basically an engineering tool, which is intended for development and testing of various reticle designs. It is also helpful for checking how OPC and phase shift features would print on the wafer. Additionally, the system can be used to study various defects discoverred by a reticle inspection systems, and test whether those defects would actually print on the wafer. However, the MSM 100 is not intended to be used as a general reticle inspection system, and lacks any of the technology required for rapid inspection of reticles.

U.S. Pat. No. 5,795,688, however, discloses a technique, for using a system such as the MSMI00 to perform an automatic inspection of a photomask. To this end, an aerial image of a portion of the photomask is acquired with the MSMI00, while a so-called "virtual stepper" software algorithm concurrently simulates a similar aerial image considering the operational conditions of a specific stepper of interest, using the reticle pattern data base. The real aerial image is compared to the simulated aerial image, and potential defects on the photomask are located. This technique actually utilizes a so-called die-to-database image processing technique, wherein the database is constituted by the simulated image. Since the image is obtained using the MSMI00, which cannot perform rapid inspection, this technique cannot be used for in-line automatic inspection of reticles progressing on a production line. On the other hand, this technique does not provide reliable results due to limitations of the simulation software. Specifically, many artificial differences between the real aerial image and the simulated aerial image would be falsely flagged as defects.

Accordingly, there is a need in the art for a reticle inspection system which would be capable of "conventional" reticle inspection in conjunction with Aerial image inspection. Moreover, the system would preferably be also capable of detecting particles on the reticle.

SUMMARY OF THE INVENTION

The present invention provides the advantages of automatic optical inspection of reticles utilizing the laser spot illumination, incorporating a novel optical inspection method and system simulating the operation of a specific stepper and specific resist.

It is a feature of the present invention that it can be constructed by easily modifying any conventional inspection system utilizing a flying spot scanning of the reticle under inspection.

The present invention utilizes the capabilities of conventional inspection systems to provide inspection using high resolution imaging of the reticle. Additionally, the inventive system is capable of inspecting the reticle using aerial imaging.

According to another embodiment, the above aperture or a second aperture is inserted into the beam's path to emulate the effects of the photoresist in lithographic process.

According to another embodiment, the shape of the illumination beam is modified from a Gaussian to a flat-top shape.

According to yet another embodiment the system is made to go out of focus or move some optical elements from their previous location to effectively expand the beam on the reticle.

According to one embodiment, a rotating scattering disk is inserted at a plane where the optical beam has a very small instantaneous diameter so that it shall reduce the time and spatial coherence of the beam on the reticle.

According to another embodiment, an aperture is inserted in the illumination channel, so that the numerical aperture of the illumination objective may be desirably adjusted. By utilizing such an aperture which also has the properties of a beamshaper, the profile of the incident beam may be changed from a gaussian to, for example, a flat-top. The collection channel also includes an aperture accommodated in front of the detector for adjusting the numerical aperture of the collection objective. In other words, by appropriately selecting the illumination and collection apertures, coherence of light in the inspection system can be adjusted to that of a selected exposure tool.

There is thus provided according to one aspect of the present invention, a system for automatic optical inspection of a reticle to be used in a selected exposure tool operating with a selected frequency of light and a selected coherence of the light, the system operating in a direct inspection mode and an aerial imaging mode, the system comprising:

a scanning apparatus scanning the reticle with a flying spot of a light beam and producing light components transmitted through the reticle;

an illumination objective positioned in the path of the flying spot and having an inherent numerical aperture for high resolution illumination;

an aperture selectively insertable in the path of the flying spot to modify the effective numerical aperture of the illumination objective during aerial imaging mode;

an aperture in the detection unit receiving at least the transmitted light components and generating data representative thereof.

Preferably, the analysis of the data representative of the at least transmitted light components includes the comparison of data representative of at least some of the successively scanned features on the reticle to each other. This is the so-called "die-to-die" signal processing technique.

The aperture may be an off-axis aperture, e.g., quadrupole. The illumination aperture may comprise beam-shaping properties, being, for example, a diffractive optical element providing a flat-top beam profile. Preferably, the aperture reduces the numerical aperture of the illumination by about a factor of four, thereby simulating the lower numerical aperture of a stepper.

Preferably, the first directing assembly comprises a set of different apertures. Accordingly, the system can resemble the operation of a different stepper of interest by selecting the illumination aperture type.

The second light directing assembly includes a, light collection aperture, which preferably provides the collection numerical aperture of for example 1.2–0.2.

The detection unit comprises at least one detector accommodated in the optical path of light transmitted through the reticle, which is preferably a photomultiplier tube (PMT).

The system may additionally utilize a dark-field inspection. To this end, the detection unit comprises at least one additional detector accommodated so as to collect light scattered from the illuminated spot on the reticle.

Additionally, to speed up the inspection, the system may utilize a so-called multispot scanning technique. For this purpose, the scanning apparatus also includes a beam splitter means for splitting the primary laser beam into at least two beams, thereby providing at least one additional scanning beam. In this case, the detection unit comprises at least one additional detector for receiving light components transmitted through a spot illuminated by the additional beam and a lens to separate the two beams to the two detecting elements.

According to another aspect of the present invention, there is provided a method for the automatic optical inspection of a reticle to be used in a selected stepper operating with a selected frequency of light, a selected coherence of the light, and a selected type of resist, the method comprising the steps of:

(a) scanning the reticle with a flying spot of a laser beam having said selected frequency;

(b) passing the incident laser beam and the transmitted light components through first and second light directing assemblies, respectively, thereby adjusting said selected coherence of the light;

(c) collecting at least the transmitted light components and generating data representative thereof, and (d) analyzing said data and generating data indicative of defects on the reticle.

More specifically, the present invention is used for inspecting the reticles used for patterning wafers during the photolithography process, and is therefore described below with respect to this application. It should be appreciated that the terms "reticle" and "mask" are used herein interchangeably.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
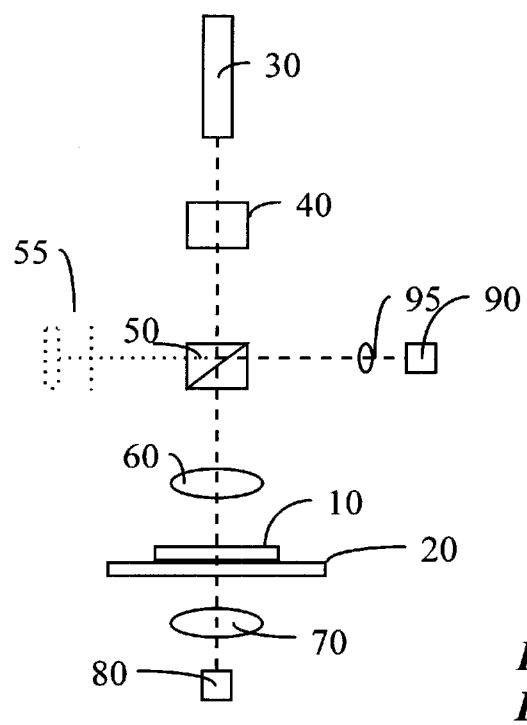
FIG. 1 schematically illustrates a system according to the prior art.
Figure 2:
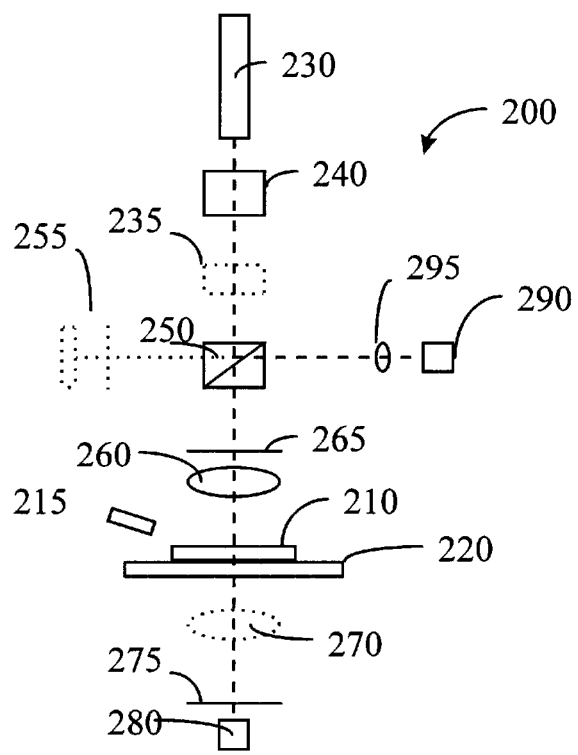
FIG. 2 schematically illustrates the main components of an optical inspection system according to one embodiment of the invention.

FIG. 2 depicts an exemplary optical inspection system, 200, according to an embodiment of the present invention. The embodiment of FIG. 2 retains many of the elements of the system of FIG. 1 and, therefore, similar elements are designated by the same character preceded by numeral "2." Due to the special construction of this embodiment, the system of FIG. 2 can be operated in at least two modes: conventional inspection mode and aerial imaging mode. In the conventional inspection mode the same elements as in FIG. 1 are employed to perform conventional inspection, i.e., using a flying spot to obtained a high resolution transmission image of the reticle and compare the image to a database or perform a die-to-die comparison.

As is known and understood from FIGS. 1 and 2, in a "flying spot" system the illumination optics has high NA, high resolution characteristics, so that a small spot is illuminated on the reticle. Then, a sensor, such as a PMT collects all the light it receives and the reticle is sampled periodically. The size of the spot and the sampling time determines the pixel size and resolution. This is in contrast to imaging optics, such as in the MSM100, wherein the illumination optics is of low resolution, but the collection optics is of high resolution and controls the pixel size and resolution.

The novel use of the system to perform aerial imaging mode will be described below.

Preliminarily, it should be noted that the light source 230 should preferably operate at a wavelength comparable to that typically used in a stepper of interest. For example, a mercury arc lamp may be used for i-line at 265 nm for 0.50–0.30 micron design rule technology, while a laser (e.g., krypton or argon excimers) at the DUV range for 0.25–0.08 design rule technology. This will improve the resolution in both the conventional and aerial imaging inspection modes. Additionally, using a wavelength comparable to that used in the photolithography tool would result in a more "realistic" aerial image.

As shown in FIG. 2, an aperture 265 can be selectively placed so as to selectively alter the effective NA of objective lens 260 (this would be generally referred to as $NA_{ill}$). In general, the objective lens 260 is of a relatively large numerical aperture (e.g., 0.6) selected to provide high resolution when aperture 265 is removed, so as to provide maximum resolution during the conventional inspection mode. However, when aerial mode is used, it is desired to match the $NA_{ill}$ of the inspection system to that of the exposure tool, e.g., 0.12. Thus, the aperture 265 reduces the effective $NA_{ill}$ from 0.6 to 0.12.

Figure 3A:
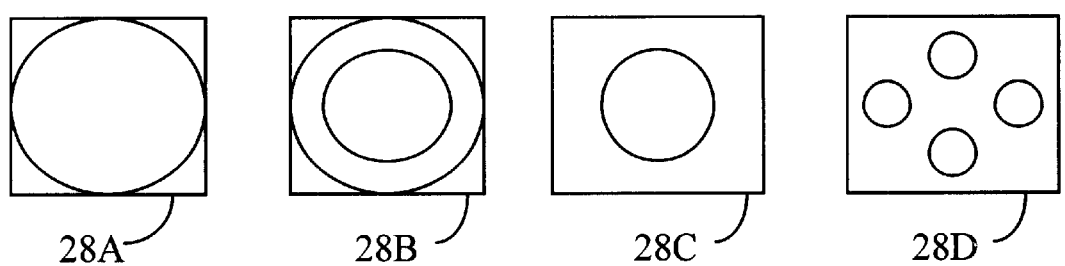
FIG. 3a illustrates a set of different illumination apertures suitable to be used in the system of FIG. 2.

As shown in FIG. 3a, a set of different apertures may be provided—four in the present example, 28A, 28B, 28C and 28D. The apertures 28A–28C are annular-shaped apertures and the aperture 28D is a quadrupole off-axis aperture enabling the enhancement of depth of focus (DOF). A selected one of these apertures can be inserted in the optical path of the laser beam $B_0$. Of course, depending on the specific illumination desired, other apertures may be used. A modified aperture or a second one may be used to change the spot shape so that the image shall emulate the effects of the photoresist as well.

Figure 3B:
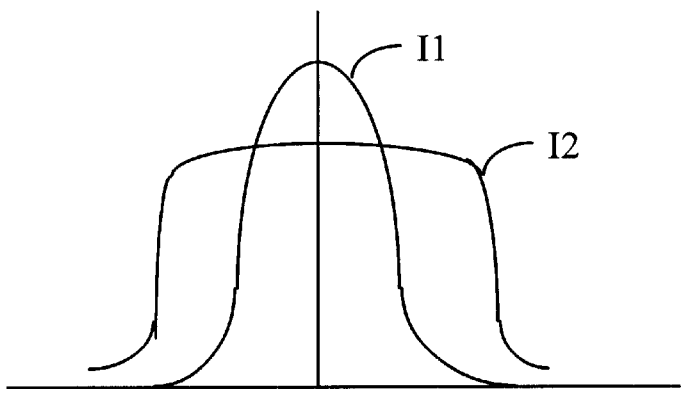
FIG. 3b graphically illustrates the main principles of an apodization aperture affecting the profile of a laser beam suitable to be used in the system of FIG. 2.

Additionally, it is desired to change the shape of the light beam to more closely resemble an exposure tool. To that effect, the illumination aperture 265 may be a diffractive optical element or a proper apodization aperture affecting also the shape of the incident beam. Preferably, the aperture 265 provides a flat-top beam, i.e., a beam with uniform intensity distribution over the cross section of the beam. FIG. 3b shows profiles $I_1$ and $I_2$ of the laser beams $B_0$ at the reticle plane (i.e., the inspection plane) with and without the proper apodization of aperture, respectively. As known, the primary laser beam has a Gaussian intensity distribution, profile $I_1$. To convert a Gaussian beam into a flat-top beam having profile $I_2$, the aperture 265 may be designed like a diffractive optical beam shaper that changes the propagation phase patterns prior to diffraction focusing. This beam shaper is one of general classes of diffractive optical elements, which can be fabricated using computer-generated holograms, photolithography and ion etching or other methods.

Generally, there is a great variety of beam-shaping techniques aimed at converting a Gaussian beam into a flat-top beam. Directly truncating the Gaussian beam with an aperture is a straightforward approach. The Gaussian beam can be attenuated with a neural density filter or an electro-optical device having a suitably controllable transversal transmittance profile. A binary optical beam shaper on interlace infraction gratings converts an incident Gaussian beam into an approximately 1-D sine-square function beam or a 2-D Bessine-square function beam in its near field and then generates a flat-top beam in its far field. Another beam-shaping technique is based on a redistributing the energy of a Gaussian beam with prisms, or aspheric reflective mirrors or aspheric lenses.

Also shown in FIG. 2 is collection aperture 275, for adjusting the effective collection numerical aperture $NA_{col}$. Typically, the aperture 275 is designed to reduce the collection numerical aperture of a conventional flying spot based inspection system to the stepper associated value of about 0.15. A condenser lens 270 is optionally used to collect the light and direct it to the light sensor.

As can be appreciated, when the apertures 265 and 275 of the system of FIG. 2 are inserted into the beam's path, the effective optics of the system resembles the optics of an exposure tool, except that the system still scans the reticle using a flying spot. Consequently, the optics thus modified can be advantageously used to obtain an aerial image of the reticle, by scanning the entire reticle in a serpentine manner. The aerial image can then be compared to a modified database or evaluated in a die-to-die manner. In operation, the user may wish to inspect the entire reticle in the conventional mode, then switch to the aerial imaging mode and inspect the entire reticle in an aerial imaging mode. Alternatively, since the design of the reticle is known, the user may wish to use the aerial imaging mode only in areas having dense features, dense OPC's, or phase shift features. Additionally, the user may wish to use aerial imaging mode to re-visit areas indicated as suspect of having defects during the conventional inspection mode.

Figure 4:
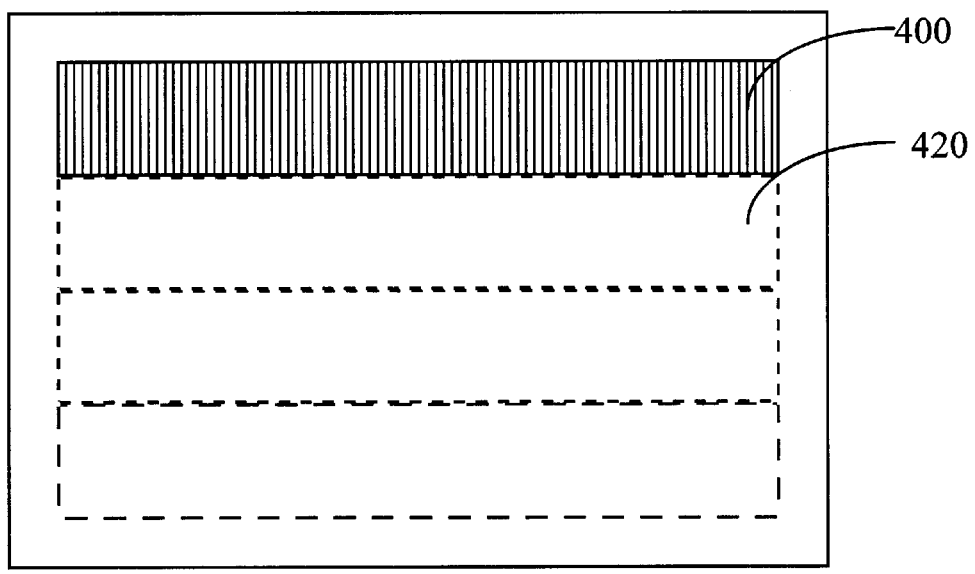
FIG. 4 schematically illustrates the operation of the system of FIG. 2.

In both the conventional and aerial inspection modes the reticle is scanned using a "flying spot." While such scanning is known in the art, it is summarized here for completeness. As shown in FIG. 4, scanner 240 scans the beam in the fast scan direction to scan a strip 400 of the reticle, while the stage 220 is moved in the slow scan direction to complete a field 420. Using a serpentine motion, the entire reticle can be inspected.

Returning to FIG. 2, an optical beam coherence reducer 235 is depicted as optional equipment. The optical beam coherence reducer is used in the aerial imaging mode to assist in beam shaping so as to further resemble an exposure tool. Specifically, the optical beam coherence reducer can be used in conjunction with the aperture 265 to provide exposure of the reticle that simulates the exposure provided by an exposure tool.

An optical beam coherence reducer can be made in the form of a rotating disk. It may be lightly diffusive ground or etched or milled glass as well as a diffractive diffuser with the proper scattering angle and phase shifting pattern. Preferably the disk rotates so that the surface moves in the contrary direction to the movement of the laser scanning beam. It is preferably introduced at a location where the beam is small and not in a place that is imaged on the objective lens.

To change the size of the spot, the system can simply be taken out of focus or some elements can be moved. That is, the system of FIG. 2 is equipped with a conventional suitable auto-focusing arrangement (not specifically shown), aimed at maintaining the inspection plane of the reticle in the focal plane of the objective lens 260. This is generally done by providing motion of the stage in the Z-axis. Thus, in order to provide effective expansion of the beam, the autofocus can be controlled to set the system out of focus. For example, the stage can be lowered to a specified distance below the focal point of lens 260.

Also shown in FIG. 2 is a dark field detector 215, which can be operational in either operating mode of the system. When the light beam hits a transparent area of the mask 210, the light is transmitted therethrough. On the other hand, when the light beam hits a reflective chrome area of the mask, it is reflected back and collected by the objective 260. Under these two circumstances the dark field detector detects no light and produces no signal. However, when a particle is present on either the transparent or reflective area, the light beam is scattered by the particle in various directions and some of that scattered light is detected by the dark field detector 215. Thus, a very high signal to noise ratio is generated for the detection of unwanted particles present on the mask.

Figure 5:
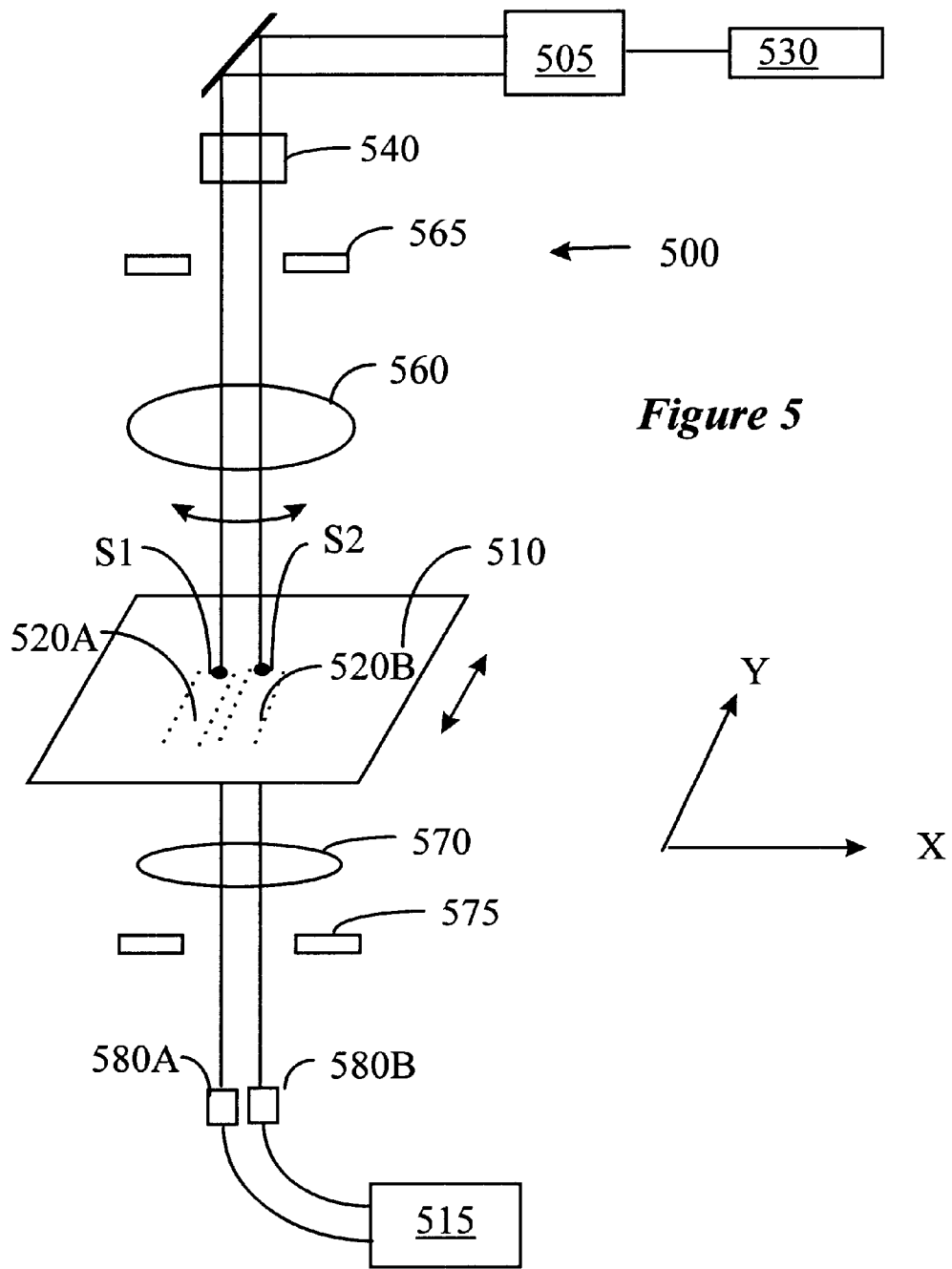
FIG. 5 illustrates the main components of an optical inspection system according to another embodiment of the invention.

Reference is made to FIG. 5, illustrating an optical inspection system 500, constructed and operated according to another embodiment of the invention. The system 500 is aimed at speeding up the inspection process by utilizing a multibeam scanning apparatus—two-beam in the present example. The scanning apparatus comprises a beam splitter and multibeam control mechanism 505 accommodated between the laser source 530 and the deflector element 540. The mechanism 505 splits the primary laser beam $B_0$ into two spatially separated beams $B^{(1)}_0$ and $B^{(2)}_0$. The beams are separated from each other along the X-axis, i.e., perpendicular to the scanning direction, and illuminate two spatially separated spots $S_1$ and $S_2$, respectively, on the reticle 510. Condenser lens 570 is accommodated in the optical path of light components $B^{(1)}_1$ and $B^{(2)}_1$, transmitted through the spots $S_1$ and $S_2$, and collected by the aperture 575. A detection unit comprises two detectors 580A and 580B for receiving these light components $B^{(1)}_1$, and $B^{(2)}_1$, respectively, and provide appropriate signal to the processor 515.

The construction of the mechanism 505 does not form part of the present invention and may be of any known kind. For example, it may include a beam splitter and a mirror accommodated in the optical path of one of the beams produced by the passage of the primary beam $B_0$ through the beam splitter. Generally, the mechanism 505 utilizes a suitable number of beam splitting means, such as prisms, partially transparent mirrors, etc., and a means for adjusting the lengths of the optical paths of the beams, e.g., a plane-parallel plate, so as to impinge onto the deflector element simultaneously. Such multibeam scanning mechanisms are disclosed, for example, in U.S. Pat. Nos. 3,725,574 and 5,210,635.

The deflection element 540, e.g., a rotating mirror or an acousto-optic deflector (AOD), deflects the beams $B^{(1)}_0$ and $B^{(2)}_0$ and cause them to scan successive spots $S_1$, and successive spots $S_2$, respectively, on the reticle 510 within spaced-apart parallel identical scan paths extending along the Y-axis. The scan paths 520A and 520B are formed by arrays of successively illuminated spots $S_1$, and $S_2$, respectively (the scanning of which is shown exaggerated in FIG. 5). At each current time, a pair of illuminated spots $S_1$, and $S_2$ is inspected, while at each relative location of the reticle relative to the lens 510, a pair of scan paths is inspected.

It should be noted, although not specifically shown, that the processor unit 515 comprises a memory and a programming means for collecting and analyzing data coming from the detectors. The analysis of the received data includes die-to-die and/or die-to-database comparison. The use of the dark-field detectors enables the reticle inspection for pattern and particle related defects simultaneously. The analysis of the received data includes also the comparison of the data representative of the dark field scattered light and data representative of the transmitted light. This transmission-to-reflection comparison is aimed at detecting the so-called "soft defects", such as particles, damaged antireflection coating, photoresist residuals, etc. Since the die-to-die and the transmission-to-reflection processing do not occur at the same time, they may be carried out by the same image processing module.

Those skilled in the art will readily appreciate that various modifications and changes may be applied to the preferred embodiments of the invention as hereinbefore described without departing from its scope defined in and by the appended claims. For example, such operational parameters of the inspection system as light frequency numerical aperture and coherence depend on those of the stepper of interest. The deflection element may be of any known kind. The illumination aperture is also of any known kind, and is preferably capable of providing a flat-top beam.

What is claimed is:

1. A system for automatic optical inspection of a photolithography substrate to be used in a selected photolithography exposure tool operating with a selected frequency of light and a selected numerical aperture and coherence of the light, and using a selected type of resist, the system comprising:
    a light source providing a light beam;
    a scanning apparatus receiving the light beam and scanning the light beam to form a flying spot over the substrate;
    an objective optics having a defined numerical aperture;
    an illumination assembly operative to adjust said defined numerical aperture to simulate said selected numerical aperture of the exposure tool;
    a light sensor receiving light transmitted through the substrate and generating data representative thereof, and,
    a processor unit coupled to light sensor to be responsive to said data for analyzing it and generating data indicative of defects on the substrate.

2. The system according to claim 1, wherein said light source comprises a continuous UV Laser.

3. The system according to claim 2, wherein said continuous UV laser is one of a doubled Argon or frequency doled and parametrically mixed solid state laser.

4. The system according to claim 1, further comprising an optical beam coherence reducer.

5. The system according to claim 1, wherein said illumination assembly comprises an illumination aperture for adjusting the said defined numerical aperture; and further comprising a collection assembly comprising a collection aperture for adjusting collection numerical aperture of propagation of the transmitted light.

6. The system according to claim 5, wherein said illumination aperture comprises an off-axis aperture.

7. The system according to claim 5, wherein said illumination aperture comprises a set of several different apertures for selectively inserting one of these apertures into the optical path of the incident light beam.

8. The system according to claim 5, wherein said illumination aperture comprises a beam shaper that changes a Gaussian profile of the laser beam to a flat-top profile.

9. The system according to claim 8, wherein said beam shaper is a diffractive optical element.

10. The system according to claim 1, wherein said detection unit comprises a photomultiplier tube accommodated so as to receive said transmitted light components.

11. The system according to claim 1, further comprising a second light sensor receiving light components reflected from the spot on the substrate and generates data representative thereof which is received and analyzed at the processor unit.

12. The system according to claim 11, wherein said second light sensor is a photomultiplier tube.

13. The system according to claim 1, further comprising a dark field light sensor receiving light components scattered from the spot on the reticle and generating data representative thereof which is received and analyzed at the processor unit.

14. The system according to claim 13, wherein said dark field light sensor is a photomultiplier tube.

15. The system according to claim 1, wherein said scanning apparatus comprises a beam splitting arrangement for splitting the generated light beam into at least 10 two spatially separated incident light beams, the system operating in an multispot scanning mode.

16. The system according to claim 1, further comprising: a condenser lens situated between said substrate and said light sensor; and aperture assembly for adjusting the effective numerical aperture of said condenser lens.

17. The system of claim 16, wherein said aperture assembly comprises a plurality of apertures selectable for adjusting the effective numerical aperture.

* * * * *